(12) United States Patent
Warhurst et al.

(10) Patent No.: US 6,663,334 B2
(45) Date of Patent: Dec. 16, 2003

(54) RANDOM ACCESS STORAGE AND RETRIEVAL SYSTEM FOR MICROPLATES, MICROPLATE TRANSPORT AND MICROPLATE CONVEYOR

(75) Inventors: Julian D. Warhurst, Ashland, MA (US); Andrew F. Zaayenga, Martinsville, NJ (US); Paul Quitzau, Blackstone, MA (US)

(73) Assignee: TekCel Inc., Hopkinton, MA (US)

( * ) Notice: Subject to any disclaimer, the term of this patent is extended or adjusted under 35 U.S.C. 154(b) by 0 days.

(21) Appl. No.: 10/196,043

(22) Filed: Jul. 16, 2002

(65) Prior Publication Data

US 2003/0059287 A1 Mar. 27, 2003

Related U.S. Application Data

(63) Continuation of application No. 09/771,112, filed on Jan. 26, 2001, now abandoned.

(51) Int. Cl.[7] .................................................. B65G 1/10
(52) U.S. Cl. ......................... 414/331.14; 414/331.16; 414/331.18; 414/798.2; 414/279; 414/284
(58) Field of Search ....................... 414/331.14, 331.16, 414/331.18, 797.5, 795.2, 798.2, 279, 284

(56) References Cited

U.S. PATENT DOCUMENTS

| | | |
|---|---|---|
| 2,166,447 A | 7/1939 | Ruppenthal |
| 2,619,916 A | 12/1952 | Rainier |
| 3,788,452 A | 1/1974 | McWilliams |
| 4,096,965 A | 6/1978 | Lessnig et al. |
| 4,509,637 A | 4/1985 | Browning |
| 5,024,315 A | 6/1991 | Ward |
| 5,024,593 A * | 6/1991 | Hehl ..................... 414/331.14 |
| 5,123,533 A | 6/1992 | Uitz |
| 5,226,782 A * | 7/1993 | Rigling ................. 414/331.14 |
| 5,246,128 A | 9/1993 | Uitz |
| 5,544,996 A | 8/1996 | Castaldi et al. |
| 5,921,739 A * | 7/1999 | Keip ..................... 414/331.14 |
| 6,099,230 A | 8/2000 | Hitch |
| 6,193,102 B1 | 2/2001 | Bevirt et al. |
| 6,254,833 B1 | 7/2001 | Shumate et al. |

FOREIGN PATENT DOCUMENTS

| | | | | |
|---|---|---|---|---|
| DE | 84 4878 A | | 7/1952 | |
| JP | 58-162440 A | | 9/1983 | |
| JP | 58-162440 | * | 9/1983 | ................. 414/331 |
| JP | 5-139512 A | | 6/1993 | |
| JP | 5-139512 | * | 6/1993 | ................. 414/331 |
| WO | WO 92/02303 A1 | | 2/1997 | |

OTHER PUBLICATIONS

U.S. Patent Application Publication, Pub. No.: US 2001/0046437 A1, Pub. Date: Nov. 29, 2001 by Bramwell et al. for an Automated System for Storing or Dispensing Stackable Goods.

* cited by examiner

*Primary Examiner*—Steven A. Bratlie
(74) *Attorney, Agent, or Firm*—Cesari and McKenna, LLP

(57) ABSTRACT

An apparatus for random access storage and retrieval of a plurality of microplates is provided. The apparatus includes a plurality of microplate racks arranged in a stack. Each of the racks is mechanically engaged with a plurality of support columns and each of the columns has a plurality of locking devices corresponding to the plurality of racks. The apparatus also includes a lift, coupled to the support columns, for moving the stack or a portion thereof, and a controller, coupled to the lift and the locking devices. The controller is responsive to a signal to access a desired rack or microplate to cause actuation of one or more of the locking devices corresponding to the rack adjacent to the desired rack or microplate, followed by actuation of the lift, thereby moving a portion of the stack a sufficient distance to allow access to the desired rack or microplate.

5 Claims, 20 Drawing Sheets

STEP　　　　AWAY　　　　　　　　　　　　　　　　HOME
1
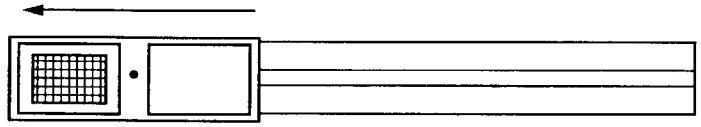
MICROPLATE TRANSPORT CARRIAGE MOVES MICROPLATE FROM
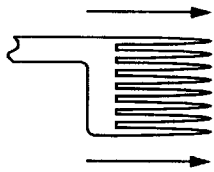
PIPETTE DEVICE AT MICROPLATE.
2
3
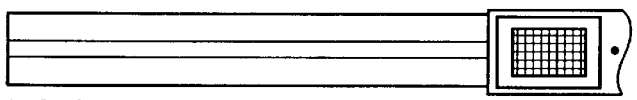
MICROPLATE TRANSPORT CARRIAGE RETURNS PIPETTED MICROPLATE TO
PIPETTE AND WAIT SEQUENCE
FIG. 15C

RANDOM ACCESS STORAGE AND RETRIEVAL SYSTEM FOR MICROPLATES, MICROPLATE TRANSPORT AND MICROPLATE CONVEYOR

This application is a continuation of Ser. No. 09/771,112 filed Jan. 26, 2001 abandoned.

BACKGROUND OF THE INVENTION

1. Field of the Invention

The present invention relates generally to the field of automated systems for handling samples in a laboratory environment and, more specifically, to systems for transporting, storing and retrieving large numbers of microplates used in applications such as high throughput screening.

2. Background Information

Industrial concerns, regulatory agencies and academic centers which conduct high throughput screening (HTS) or similar applications are faced with a problem of how to store, retrieve and transport hundreds or thousands of microplates which are necessary for such screening. While it may be generally desirable to automate these tasks as much as possible, there are numerous factors which must be taken into account for any automation effort to be successful. Human safety, system reliability, security, environmental control, and space requirements are but a few of the more important factors.

Another important aspect in designing automated systems for HTS is the ease with which one piece of equipment interfaces with another. Appropriate interfaces are necessary to avoid costly bottlenecks or delays while maintaining appropriate environmental conditions with respect to samples. In addition, it may be necessary to provide interfaces between equipment made by different manufacturers in order to accommodate the requirements of a customer's application.

SUMMARY OF THE INVENTION

In brief summary, the present invention provides a collection of components for storing, retrieving and transporting large numbers of microplates in a highly integrated and automated system. The components readily interface with each other, thus enabling a high volume of microplates to be passed among the components for desired processing or storage. In addition, one component, a microplate transport, provides a way to transport microplates to or from third party equipment which a customer may wish to use in conjunction with the present invention's components.

In accordance with one aspect of the present invention a random access storage and retrieval system for storing on the order of one thousand microplates in a very compact, highly efficient manner is provided. In a preferred embodiment, the storage and retrieval system includes a series of rectangular metal racks, each capable of storing up to 36 microplates. The racks are stacked upon one another. Each corner of each rack is mechanically engaged with a support column by way of a tongue and groove arrangement which allows the rack to be selectively locked to the four support columns by way of pneumatic pistons.

After a particular rack is locked to the support columns, a hydraulic lift raises the support columns a short distance, effectively creating a clearance immediately below the locked rack. Using an elevator attached to one side of the racks, a robotic crawler is lifted until it is approximately level with the rack below the clearance. By using a rack and pinion to move across the storage rack, the crawler is able to effectively access the entire area of the rack and either store or retrieve one or more microplates.

Once the robot has completed its operations on a particular rack, the robot is withdrawn into the elevator and lowered to its base. The hydraulic lift then lowers the support columns to their resting position and the pneumatic pistons are depressurized, thus unlocking the rack that was previously locked. A microprocessor-based controller controls the operations of the hydraulic lift, pneumatic pistons, elevator and robot.

In a second aspect of the invention, a microplate transport for moving microplates between one workstation and another is provided. In a preferred embodiment, the transport includes a carriage which is driven along a pair of rails by a servo. The carriage is capable of carrying two microplates on a turntable. Driven by a second servo, the turntable may be turned to allow a microplate to be placed in or removed from either of two holders. Sensors, located beneath and at opposite ends of the rails, work in conjunction with the servos and a controller to stop the carriage at the correct position and to turn the turntable to the correct angular position for loading or unloading the microplates.

The microplate transport is operable in accordance with any of several methods to perform different tasks. In a first method, the transport is used to move microplates from one location, referred to as the home location, to another location, referred to as the away location, for processing and, subsequently, to return the processed microplates to the home location. This method begins with the loading of the carriage with a single microplate at the home location. The carriage is driven to the away location, and the microplate is removed for processing. The carriage returns to the home location and is loaded with another microplate. The carriage is driven again to the away location and arrives with its microplate in the inboard side and an open slot in the outboard side. A microplate that was previously left for processing at the away location is now loaded into the outboard side. The turntable is turned 180° and the microplate that was last loaded at the home location is removed. The carriage then returns to the home location and the cycle begins again.

In accordance with a second method of operation, the microplate transport is used to move microplates from the home location to the away location without returning them. The transport may be used to move one or two microplates per trip.

In accordance with a third method of operation, the microplate transport is used to move a microplate from the home location to the away location, wait for a pipetting function to be performed, then return the microplate to the home location. At the away location, the turntable may be turned to bring the microplate in closer proximity to the pipettor.

In a third aspect of the present invention, a microplate conveyor for moving microplates bi-directionally between, for example, the above-described storage and retrieval system and a workstation or between two workstations is provided. The conveyor, which is typically housed within the interior of the storage and retrieval system or workstation, is laterally extendable such that it may span a distance between two adjacent cabinets. A distance on the order of several inches or more may be spanned. The conveyor employs a fixed length, endless loop drive belt which is wound, in part, around tensioning elements that are capable of moving laterally as the conveyor is extended or retracted. The tensioning elements act to take up slack in the drive belt when the conveyor is retracted and to dispense slack when the conveyor is extended. A microplate holder which rides on the drive belt is capable of carrying up to four microplates at a time and may be loaded or unloaded by robotic equipment.

BRIEF DESCRIPTION OF THE DRAWINGS

The invention description below refers to the accompanying drawings, of which:

FIGS. 15A–15C are a series of slide-shows illustrating three methods of operation of the microplate transport;

DETAILED DESCRIPTION OF ILLUSTRATIVE EMBODIMENTS

Figure 1:
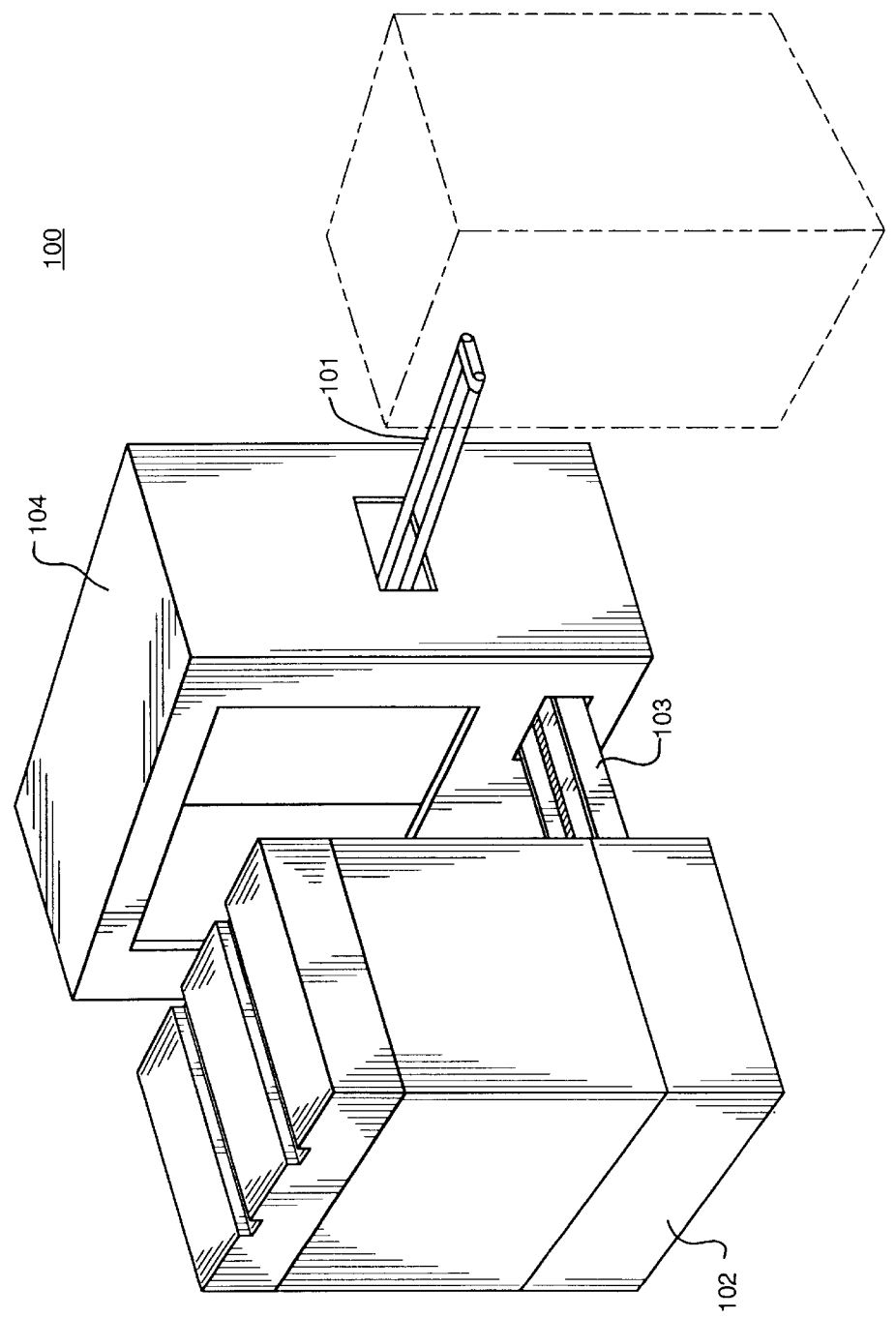
FIG. 1 is a perspective view of a random access microplate storage and retrieval system, microplate transport and microplate conveyor, all of which are constructed in accordance with preferred embodiments of the present invention.

FIG. 1 shows a laboratory environment 100 in which a series of microplate processing, transportation and storage components are integrated into a highly automated, efficient system which is well suited for HTS. It should be understood that the term "microplate" as used herein includes, but is not limited to, shallow well, deepwell, half deepwell and PCR type plates as well as minitube racks. It should also be understood that the present invention is not limited to any particular matrix size.

A workstation 104 represents any of a variety of equipment used to prepare or process (e.g., pipetting, cleaning, inspecting, etc.) microplates. Workstation 104 may represent, for example, an Assay TekBench™ sold by TekCel, Inc., the assignee of the present application. A microplate transport 101 extends from the interior of workstation 104 to a position a few feet outside of that workstation. As described in detail below in connection with FIG. 9 et seq., microplate transport 101 is used to move microplates bidirectionally between workstation 104 and a second workstation (shown in phantom) or other equipment which may be located proximate to workstation 104.

Workstation 104 is connected by a microplate conveyor 103 to a microplate storage and retrieval system 102. As described in connection with FIG. 2 et seq., storage and retrieval system 102 is capable of providing random access, high density storage of on the order of one thousand (1000) microplates. Microplate conveyor 103 operates to move microplates bidirectionally between workstation 104 and storage and retrieval system 102, as described in detail below in connection with FIG. 16 et seq.

Figure 2:
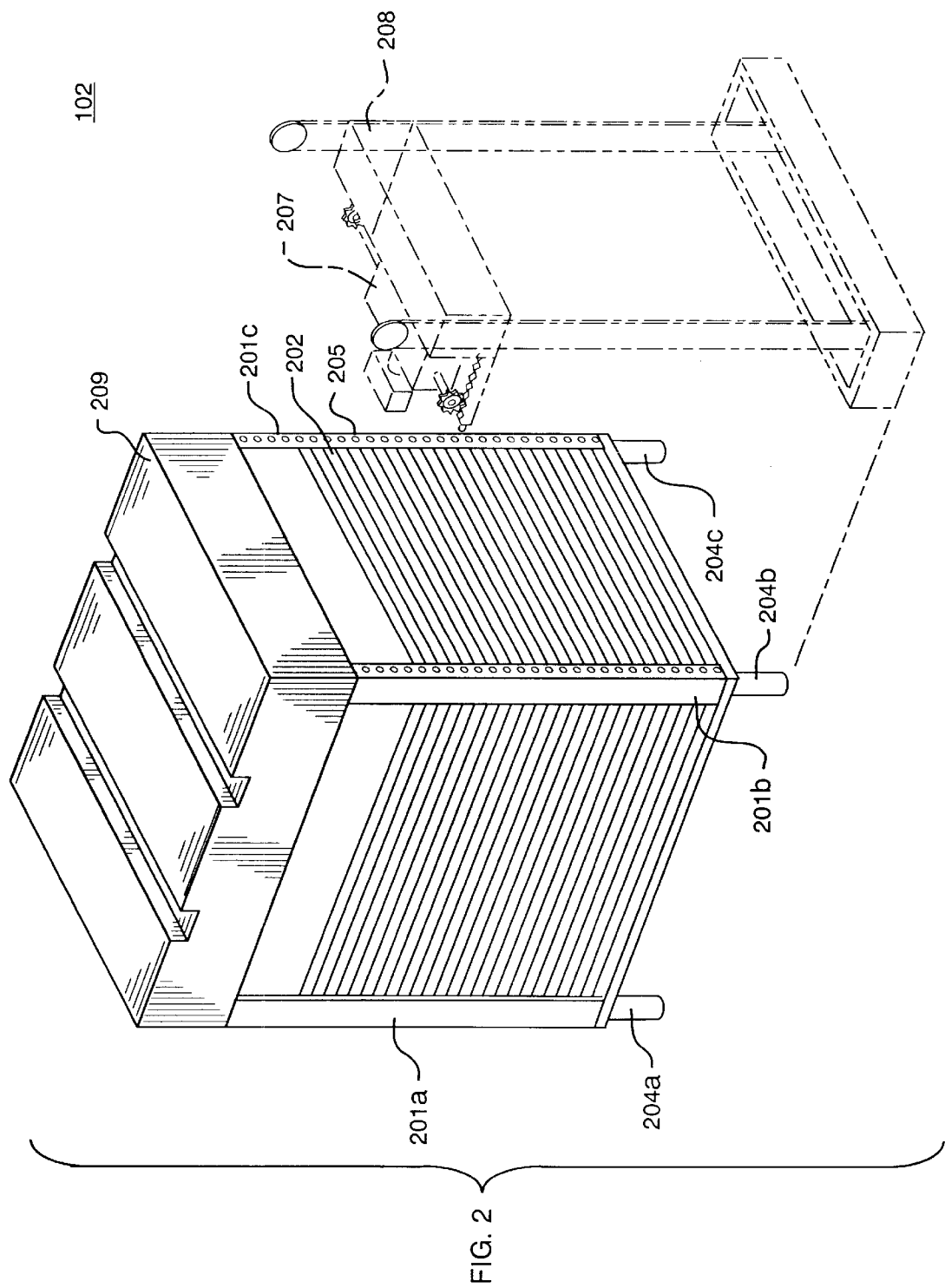
FIG. 2 is a perspective view of the storage and retrieval system, separated from other equipment, of FIG. 1.

FIG. 2 is a perspective view of the storage and retrieval system 102 with the housing removed for purposes of improved clarity. Four support columns 201a–201d are disposed, respectively, at the corners of the system. A series of microplate storage racks 202 are stacked together within the volume defined by columns 201 and a top cover 209. As may be seen more clearly in FIG. 7, each of the corners of racks 202 is mechanically engaged with the adjacent column 201 in a tongue and groove arrangement that allows the racks to both move vertically and be selectively locked to the columns.

The lower ends of columns 201 are joined with feet 204. Feet 204 each house a hydraulic lift (not visible) that is capable of lifting the entire stack of storage racks 202 by several inches. Each column 201 has a series of through holes 205 along its height. Pneumatic pistons 206 are secured to the columns 201, adjacent to each of holes 205, such that when a piston is actuated, a metal pin is driven into the hole.

A robotic crawler 207 is disposed within an elevator 208. Elevator 208 operates to lift crawler 207 to the correct height to access a particular storage rack 202. Once positioned at the correct height, crawler 207 may move laterally out of elevator 208, traverse the storage rack 202 and either store or retrieve a microplate.

Figure 3:
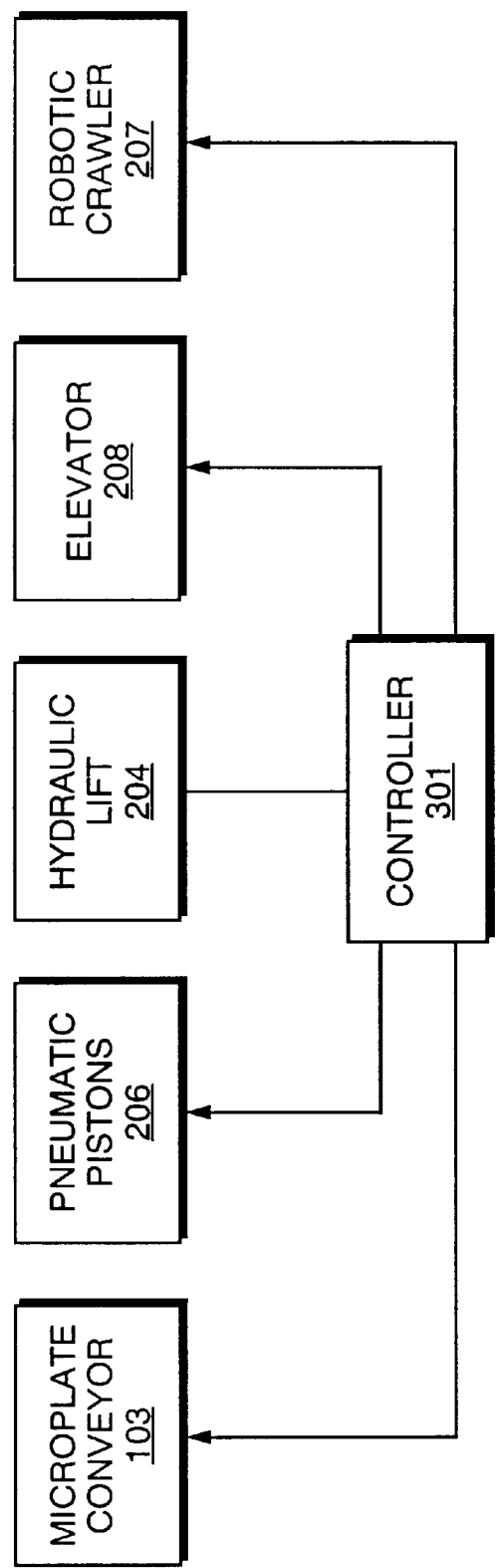
FIG. 3 is a block diagram of the control system which controls the functions of the storage and retrieval system of FIG. 2.

FIG. 3 is a block diagram showing the high level control architecture of storage and retrieval system 102. A microprocessor-based controller 301 is connected in communicating relationship with microplate conveyor 103, hydraulic lift 204, pneumatic pistons 206, robotic crawler 207 and elevator 208. A Microchip Technology 17C43 microcontroller is preferably used as a central element of controller 301, but those skilled in the art will appreciate than any of a number of commercially available microprocessors, microcontrollers or other devices could be used instead. Controller 301 may be programmed, in accordance with well known techniques and any of a variety of computer languages, to perform the microplate storage and retrieval functions described in detail below in connection with FIGS. 4–8B.

Figure 4:
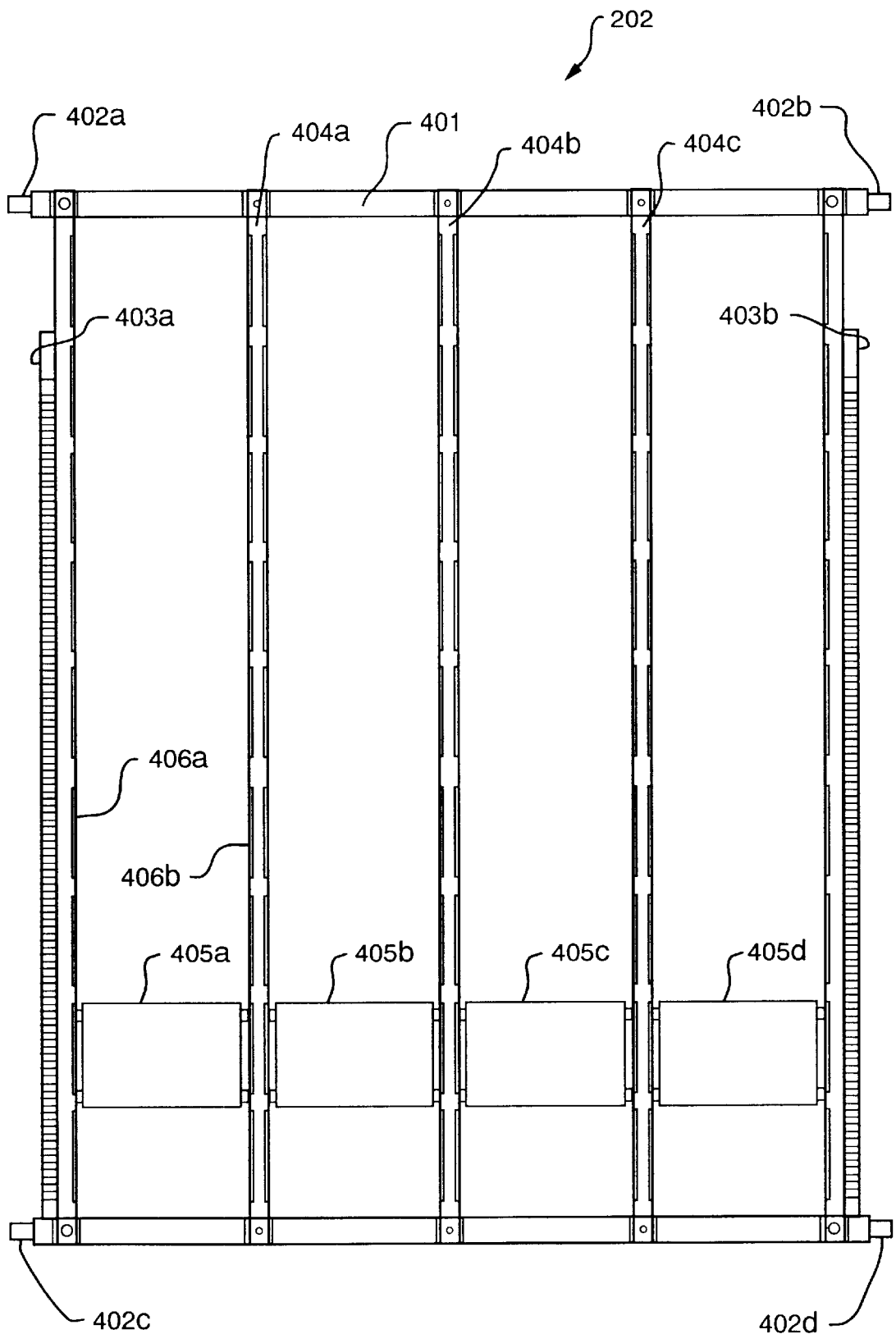
FIG. 4 is a top plan view of one of the microplate racks used in the storage and retrieval system of FIG. 2.

FIG. 4 is a top plan view of a representative one of the microplate storage racks 202 shown in FIG. 2. A rectangular frame 401 includes four tongues 402a–402d which extend, respectively, from each corner. Attached to the outside of each long side of frame 401 are (gear) racks 403a and 403b.

Spans 404a–404c, in conjunction with frame 401, provide a total of thirty-six (36) microplate storage locations, four of which are illustratively occupied by microplates 405a–405d.

Each storage location is essentially defined by a pair of oppositely disposed recesses, such as 406a and 406b, which are shaped and dimensioned to support the bottom edges of a desired type of microplate. Storage rack 202 is preferably constructed from stainless steel, but it should be understood than any of a number of other materials may be used.

Figure 5:
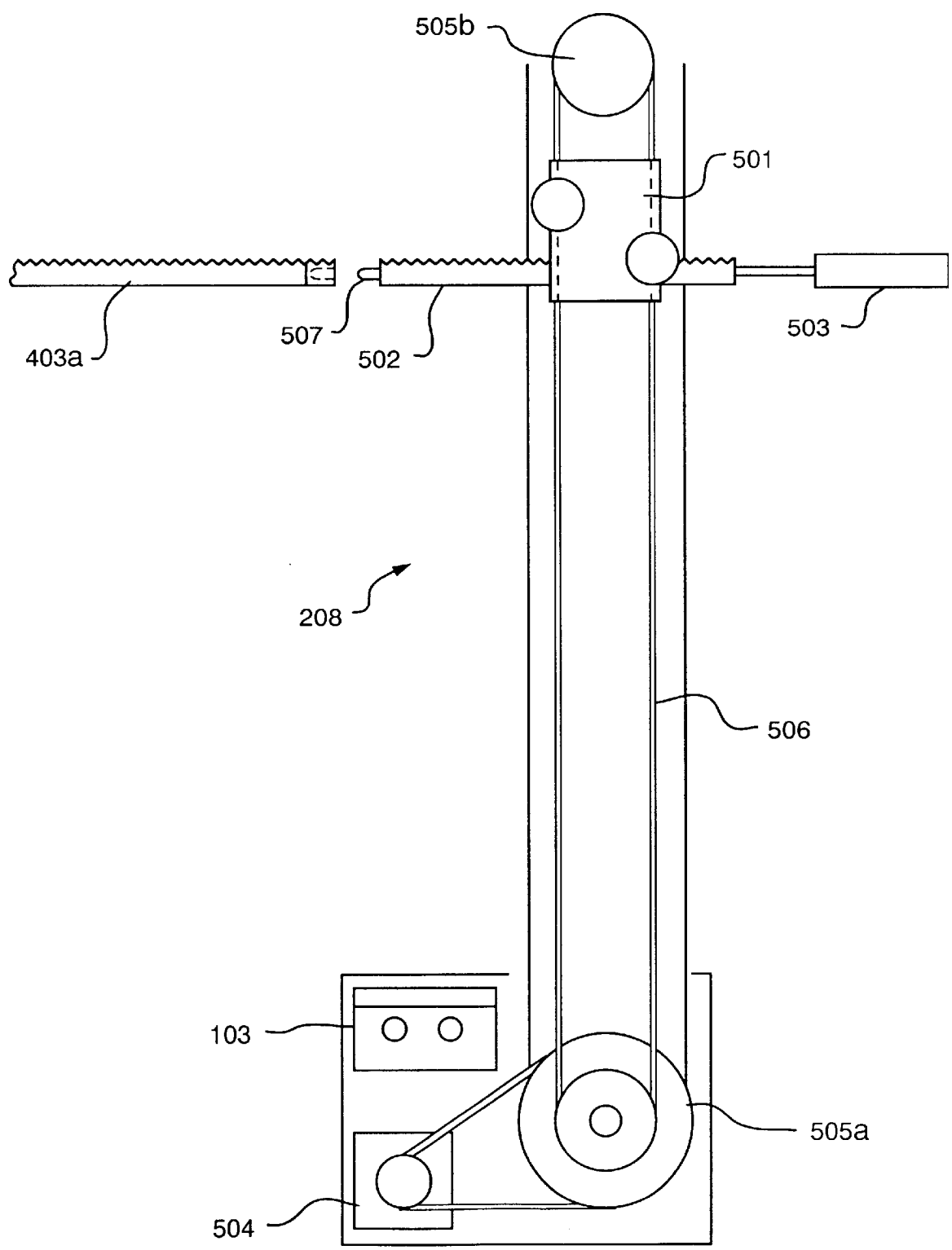
FIG. 5 is a schematic diagram of the elevator shown in FIG. 2.

FIG. 5 is a schematic diagram of elevator 208 of FIG. 2. One end of microplate conveyor 103 (FIG. 1) is visible in the base of elevator 208. A lift 501, in which robotic crawler 206 is normally housed, is propelled vertically by a combination of a motor 504, pulleys 505a, 505b and cables 506. Attached to lift 501 is a length of (gear) rack 502, which is preferably of the same type as rack 403. A piston 503 operates to extend or retract rack 502. A vane Hall effect sensor 507 is preferably located at the end of rack 502. When lift 501 is brought to the approximate height to access a particular storage rack (ie., by coarse position determination such as counting motor turns), sensor 507 is used to precisely align gear racks 403a and 502. Next, piston 503 extends gear rack 502 such that it mates with gear rack 403a, thus forming a "bridge" between lift 501 and one of storage racks 202. Crawler 207 uses the bridge to move between lift 501 and the storage rack of interest.

Figure 6:
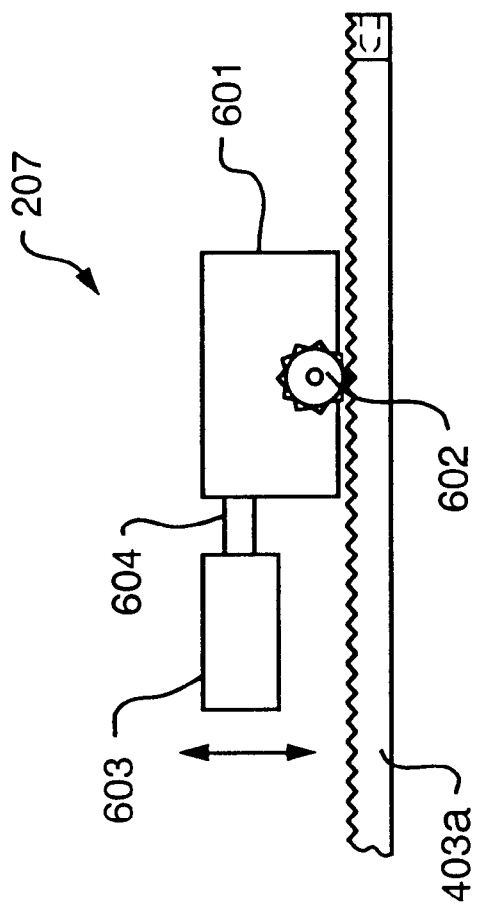
FIG. 6 is a schematic diagram of the robotic crawler of FIG. 2.

Referring now to FIG. 6, robotic crawler 207 includes a motor housing 601 and a pinion 602 which, in conjunction with rack 403a, allows crawler 207 to move along the length of a storage rack. A gripper 604 functions to carry a microplate 603 to or from a specified storage location.

Figure 7:
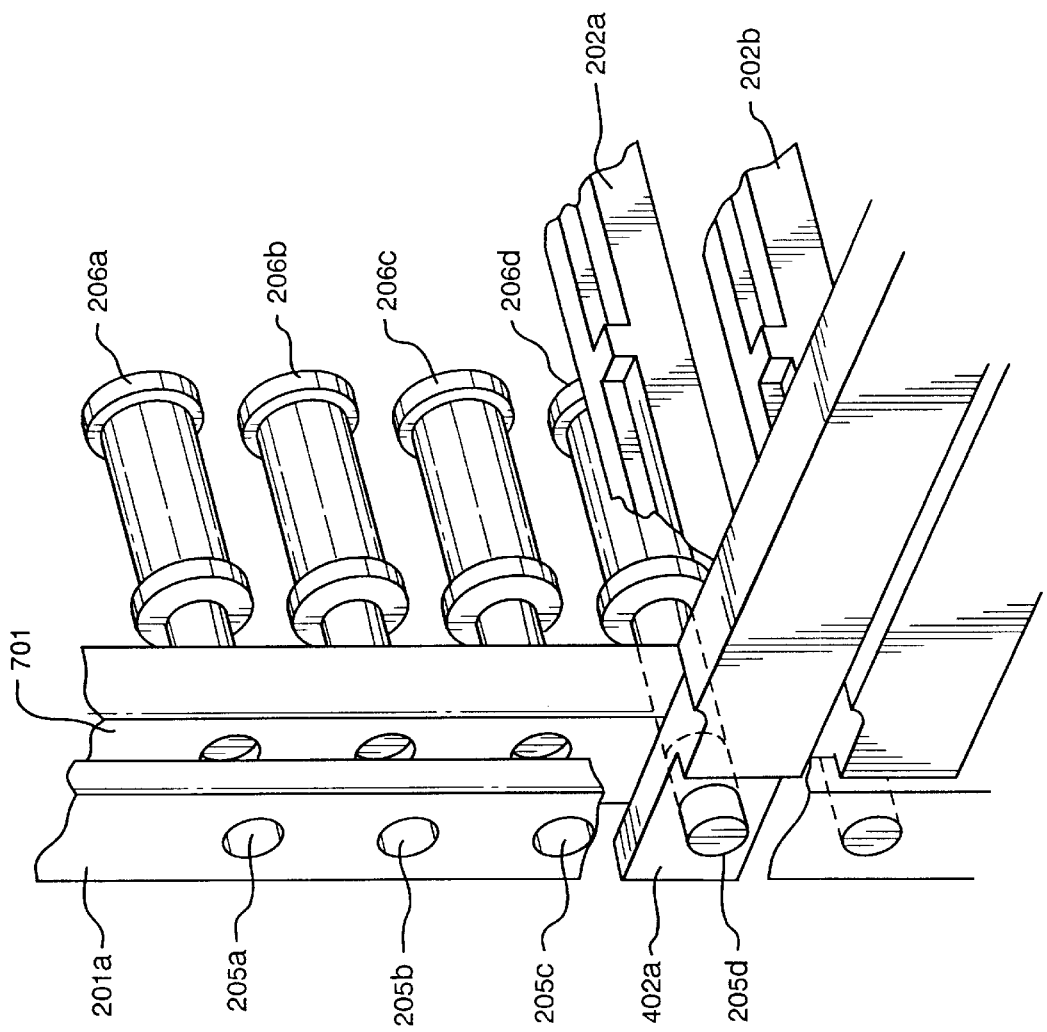
FIG. 7 is a detailed, partially cutaway view of one of the support columns and microplate rack corner structures.

FIG. 7 is a detailed, partially cutaway perspective view showing the mechanical relationship between representative ones of the support columns and storage racks. Support column 201a is essentially U-shaped in cross section and includes a slot or groove 701 which is shaped and dimensioned to receive the tongues, such as 402a, located on each corner of the storage racks 202. When any of pneumatic pistons 206 is actuated, a pin is extended through the corresponding hole 205 as well as a matching through hole in the tongue 402. In this fashion, the four corners of any storage rack may be securely locked to the support columns.

With reference now to FIGS. 5–8B, the operation of the storage and retrieval system 102 will now be described. As shown in FIG. 8A, when storage and retrieval system 102 is at rest, a vertical clearance of several inches is visible between the topmost storage rack 202c and the top cover 209 of system 102. Now, assume that an instruction is received to store or retrieve a microplate from storage rack 202b which is near the middle of the stack. The pneumatic pistons 206 which correspond to rack 202a, which is the storage rack immediately above the one of interest, are actuated and lock rack 202a to the support columns 201. Now, the hydraulic lifts located in feet 204 are actuated, thus lifting the locked storage rack 202a, as well as all of the racks located above the locked rack, by several inches.

Figure 8B:
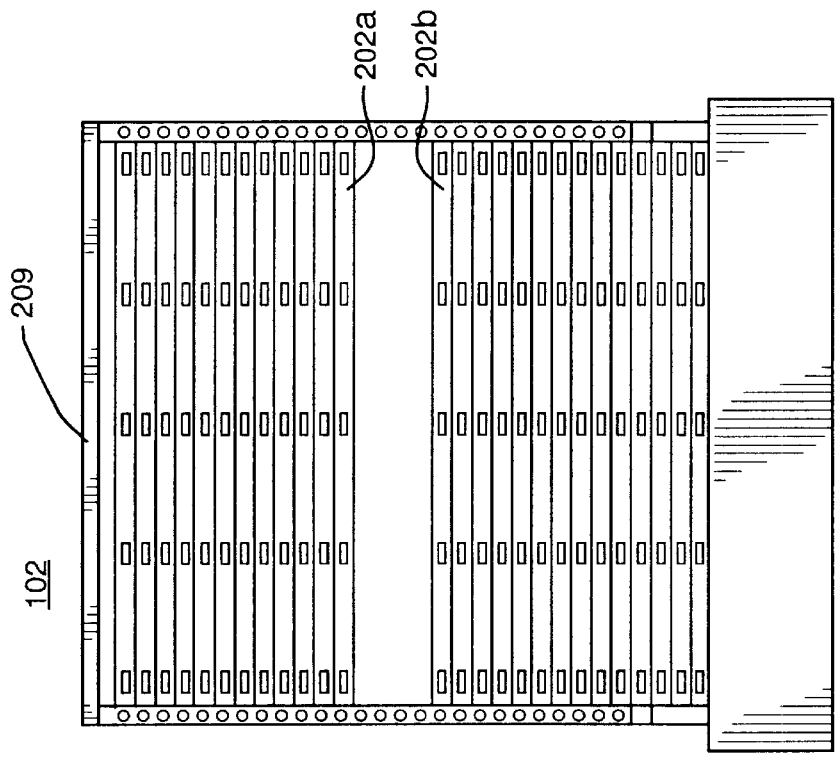
FIGS. 8A and 8B are side elevations showing the storage and retrieval system in operation.
Figure 8A:
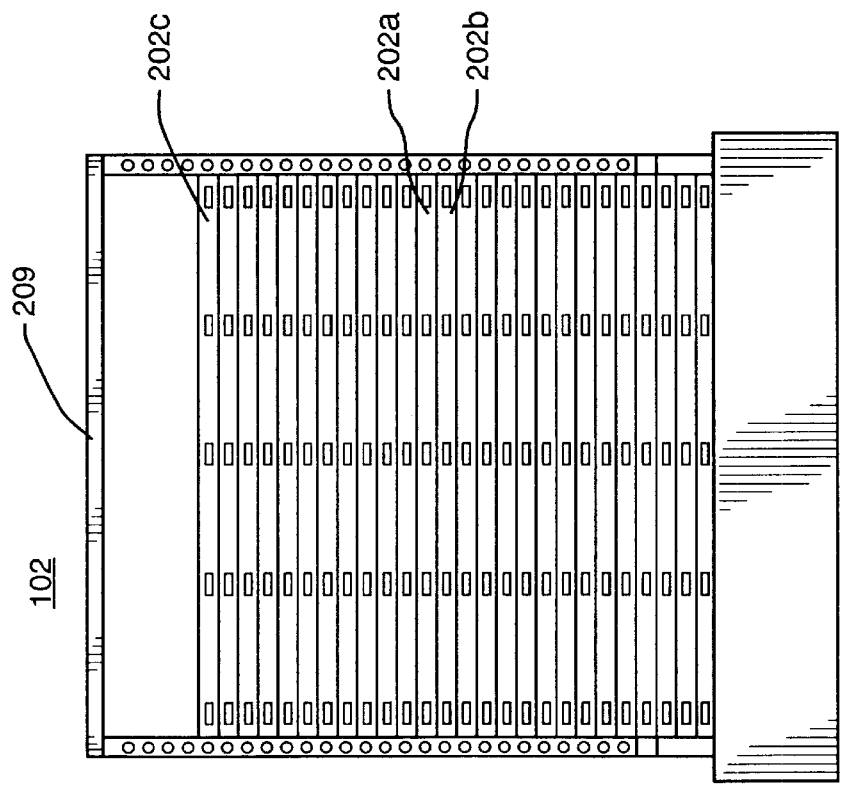

The result, as shown in FIG. 8B, is the creation of a vertical clearance of several inches immediately above rack 202b where it is desired to store or retrieve a microplate. That clearance is sufficient for crawler 207 to perform the necessary storage or retrieval function. Once the crawler 207 has completed its functions and returned to elevator 208, the hydraulic lifts are released and the system 102 returns to its original resting position. Crawler 207 may then, for example, descend in lift 501 to the base of elevator 208 and transfer a microplate to conveyor 103 for further transportation. Conversely, crawler 207 may pickup microplates arriving on conveyor 103 and store them in appropriate locations among racks 202. In this fashion, large number of microplates may be stored or retrieved and passed to or from other equipment in a fully automated way without manual intervention.

Figure 9:
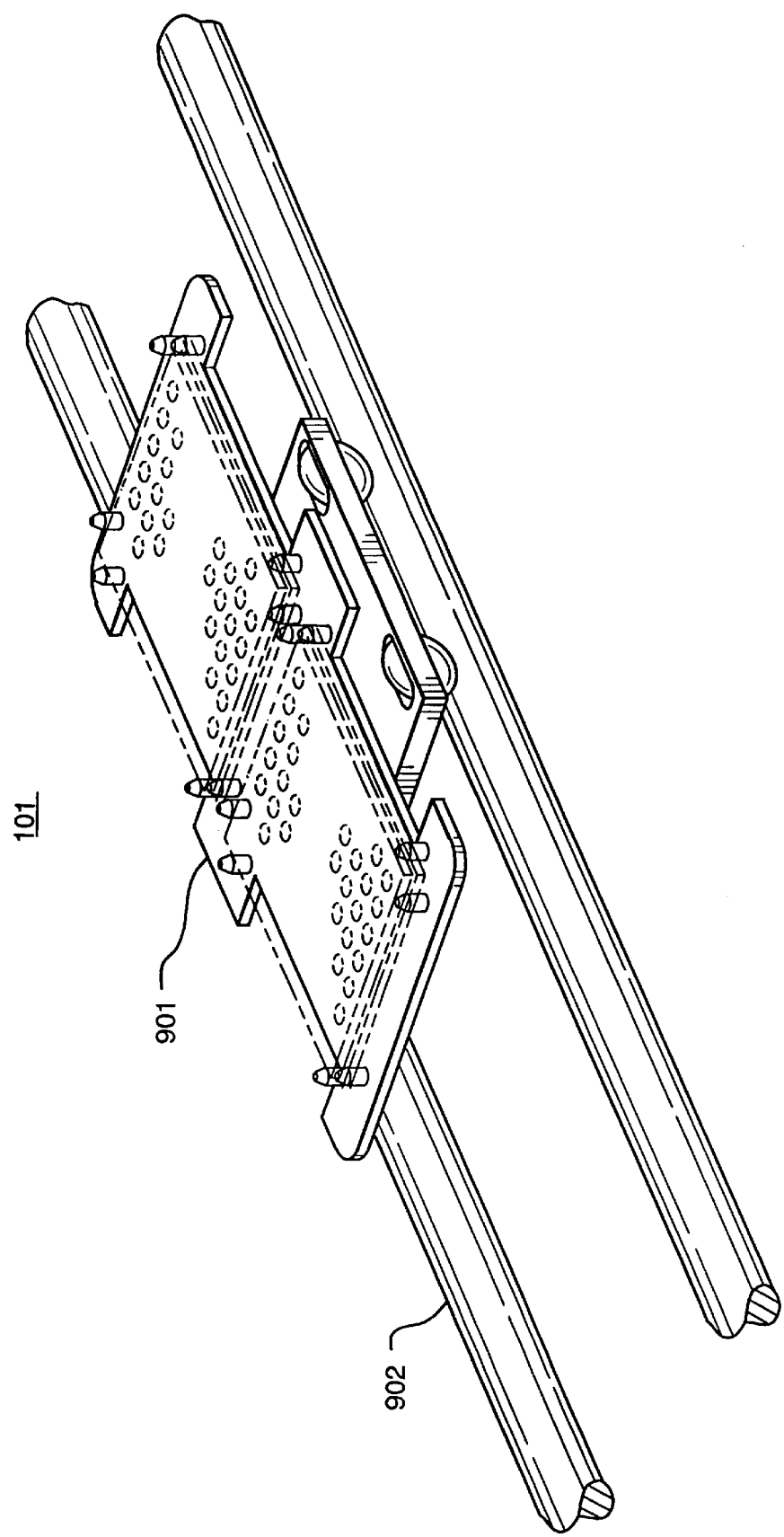
FIG. 9 is a perspective view of the microplate transport, separated from its cabinet, shown in FIG. 1.

Referring to FIG. 9, a microplate transport assembly 101 is shown separated from its cabinet. The microplate transport assembly 101 includes a microplate transport carriage (carriage) 901 and a microplate transport rail assembly 902. The carriage 901 is used to hold one or more microplates for transport from one station to another. The carriage 901 moves along the microplate transport rail assembly 902.

Figure 10:
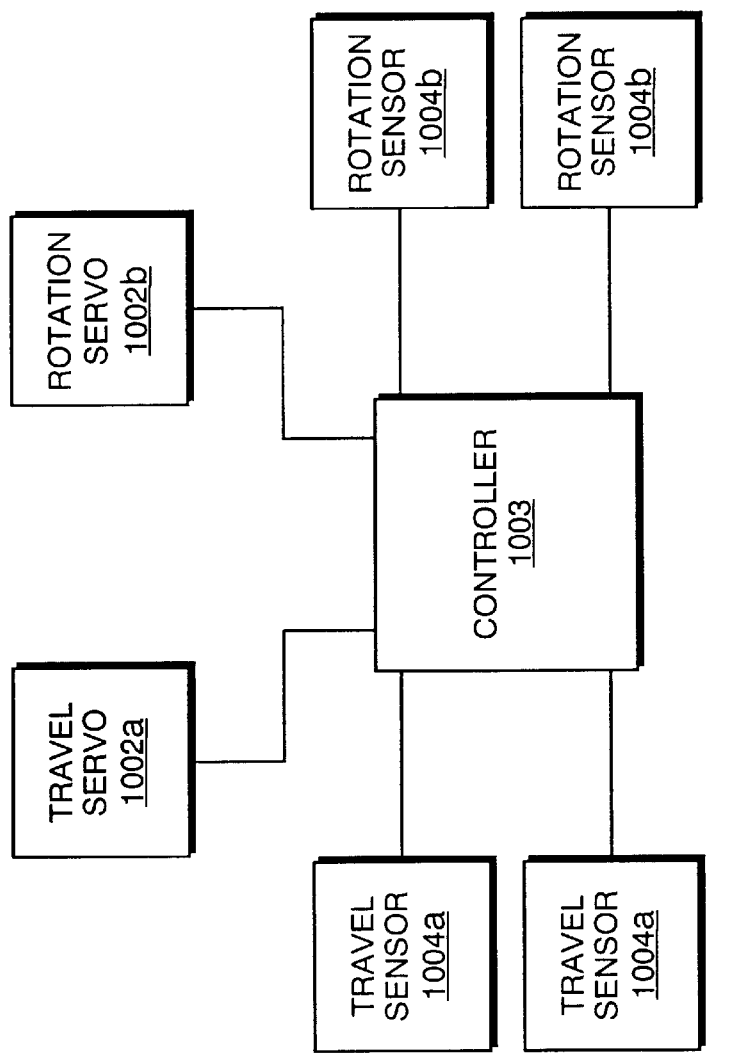
FIG. 10 is a schematic of the motors and controller which control the movements of the microplate transport.

Referring to FIG. 10, a schematic diagram of the microplate transport assembly's 101 drive system 1001. The drive system includes two servos 1002a and 1002b. Travel servo 1002a functions to move the carriage 901 along the microplate transport rail assembly 902. Rotation servo 1002b operates to rotate a portion of the carriage 901. The drive system 1001 also includes a controller 1003 used to manage the drive servos 1002a and 1002b and to receive input signals from sensors 1004a and 1004b. Travel sensors 1004a detect the position of the carriage 901 while rotation sensors 1004b detect the orientation of the rotatable portion of the carriage 901. Sensors 1004a and 1004b are each disposed on the ends of microplate rail assembly 902 in positions to be shown in a later figure. The controller 1003 receives positional data from travel sensors 1004a and rotation sensors 1004b. Using the positional data from sensors 1004a and 1004b, the controller commands the servos 1002a and 1002b according to input from an external source such as a host computer (not shown). Sensors 1004a and 1004b are preferably optical type, capable of resolving changes in ambient light intensity.

Figure 11:
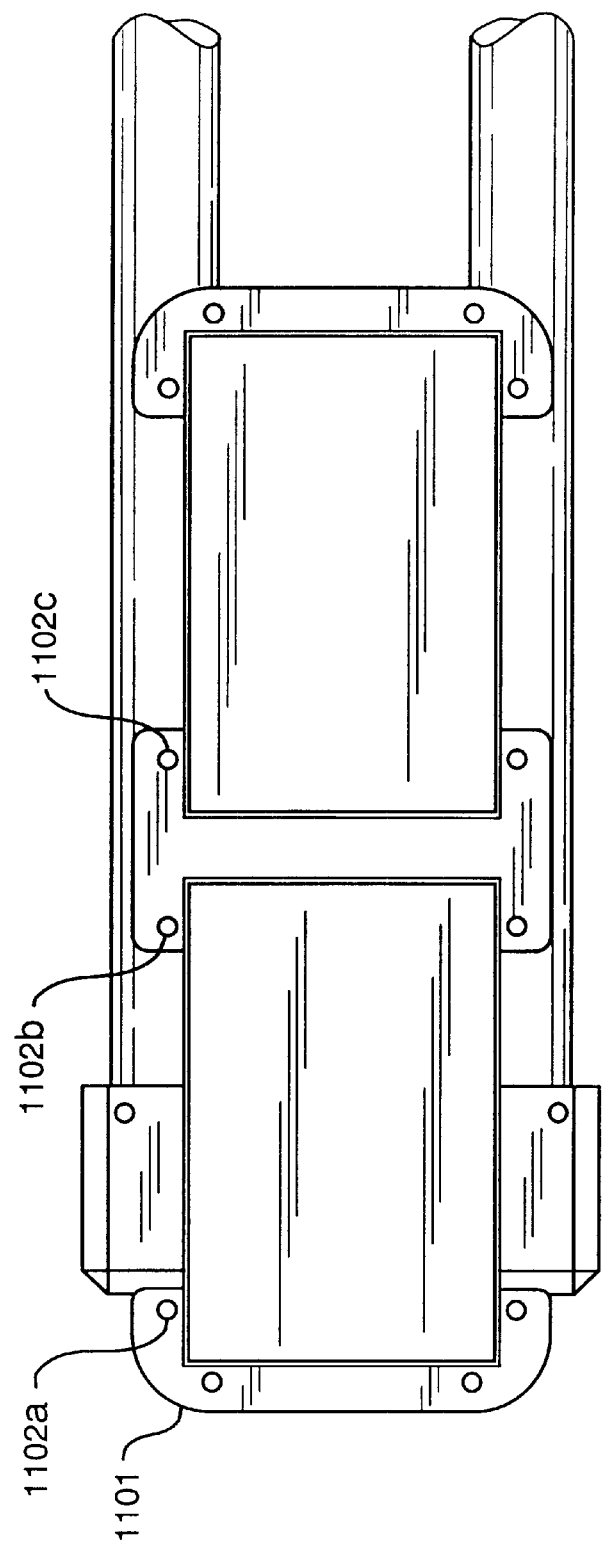
FIG. 11 is a top plan view of the carriage shown in FIG. 9.

Referring to FIG. 11, a top plan view of the carriage 901 that comprises a rotary platter 1101, and alignment pins 1102a–1102c. The carriage 901 also includes other components that may be best seen in subsequent figures. The rotary platter 1101 holds up to two microplates during transport on the microplate transport carriage 901.

Microplates are held into place on the rotary platter 1101 by the alignment pins 1102. The alignment pins 1102 protrude from the rotary platter 1101 and are situated around the exterior of the rotary platter 1101 providing a frame for a microplate. The frame provided by the alignment pins 1102 serves to hold the microplate securely in place during transport. Rotary platter 1101 may hold, in the illustrated embodiment, up to two microplates at one time. It is recognized that a rotary platter holding more than two microplates may be desirable where a large number of microplates must be transported.

The general operation of the carriage 901 will now be briefly described. The rotary platter 1101 may rotate 180° during operation in order to present the microplates to, for example, a robotic handler (not shown) for loading or unloading. During transport, the rotary platter 1101 is preferably kept in the position shown in FIG. 11 so that the microplates do not extend outside the rails. Upon reaching the destination a leading microplate may be off loaded from the rotary platter 1101. Once the leading microplate has been off loaded, the rotary platter 1101 may rotate 180° in order to present the remaining microplate for off loading. This rotation is performed by operation of the rotary servo 1002b.

Figure 12:
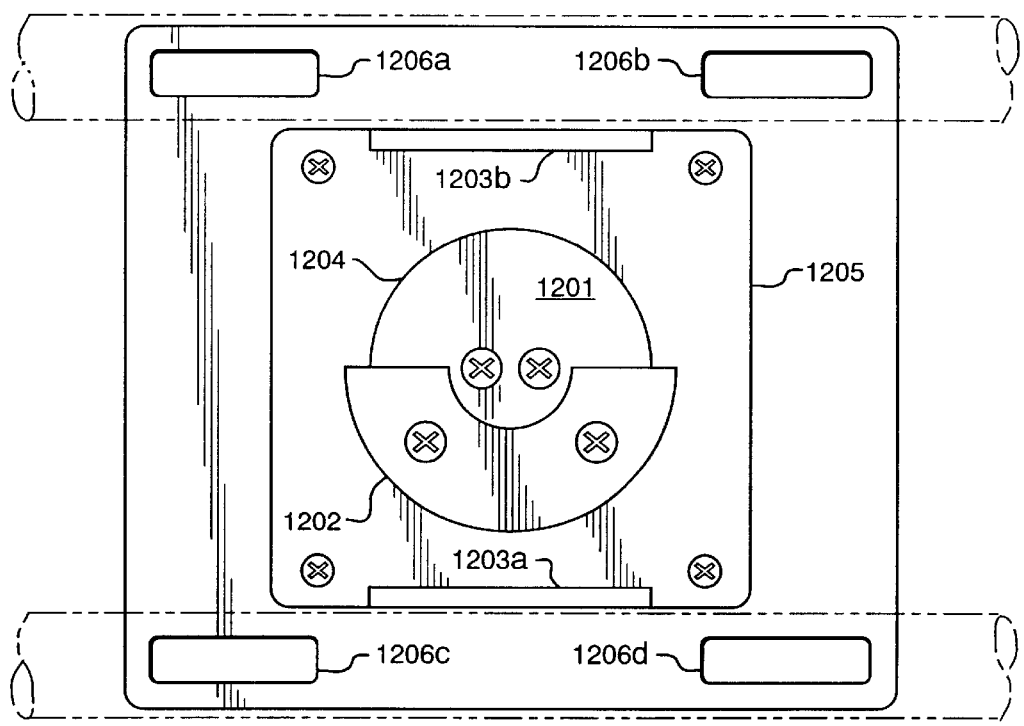
FIG. 12 is a bottom plan view of the carriage shown in FIG. 9.

Referring to FIG. 12, a bottom view of the carriage 901 is shown. A rotary mount 1201 is disposed in the center of the carriage 901. A rotary flag 1202, in the shape of one half of an annular ring is spaced from and attached to rotary mount 1201. Travel flag 1203a and 1203b are rectangular tabs which extend vertically from base plate 1205. The cables which connect carriage 901 to servos 1002a and 1002b have been omitted for improved clarity. The rotary mount 1201 operates as the base for the rotary platter 1101. A cylindrical bearing 1204 of the rotary mount 1201 is also illustrated. The bottoms of four carriage wheels 1206a–1206d are also visible.

Rotary flag 1202 and travel flags 1203a and 1203b operate, in conjunction with the rotation sensors 1004b and travel sensors 1004a to determine rotation of the rotary platter 1101 and movement of the carriage 901, respectively. Rotation sensors 1004b generate a signal indicative of the orientation of the rotary platter 1101 by sensing the movement of the rotary flag 1202. That is, rotary flag 1202 creates light-to-dark and dark-to-light transitions when it passes over rotation sensor 1004b. Thus, controller 1003 determines the orientation of the rotary platter 1101 by reading the corresponding transitions in the rotation sensor's output signal.

Similar to the rotation sensor 1004b, travel sensors 1004a generate output signals indicative of the carriage's lateral position in response to ambient light changes. In essence, the travel servo 1002a drives carriage 901 along the microplate transport rail assembly 902 until one of the travel flags 1203 causes a change in the output signal of one of the travel sensors 1004a. Preferably, carriage 901 is decelerated before actually reaching one of the travel sensors 1004a by using controller 1003 to resolve course position by duration of servo drive or some other available notice.

Figure 13:
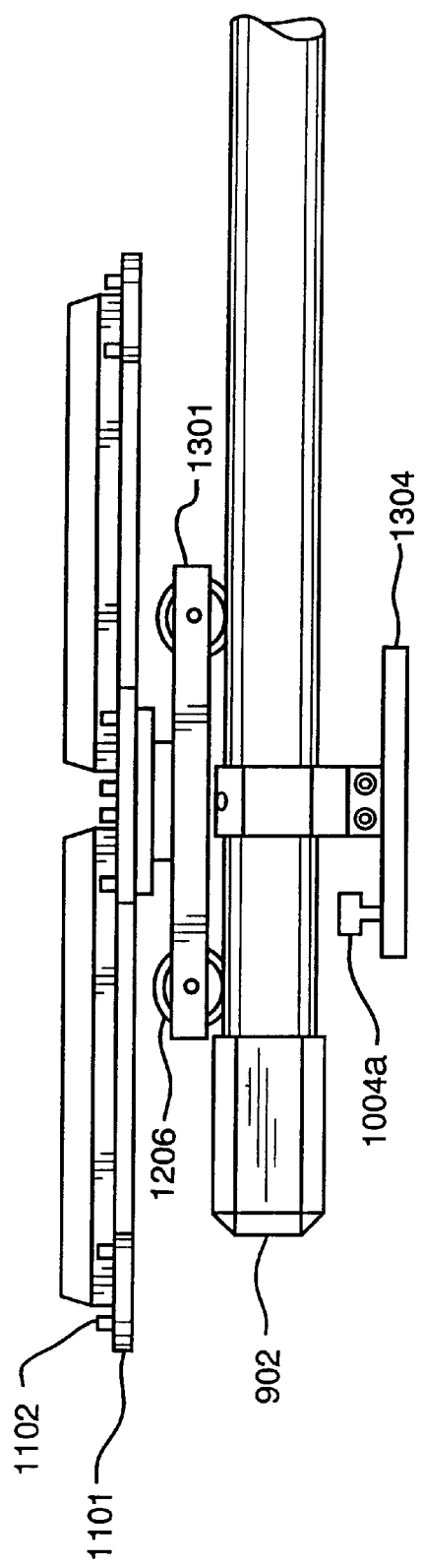
FIG. 13 is a side elevation of the carriage and rails.

Referring to FIG. 13, a side view of the carriage 901 and the microplate transport rail assembly 902 is shown. In addition to the rotary platter 1101, alignment pins 1102, rotary mount 1201, rotary flag 1202, and travel flag 1203, a carriage body 1301 and the carriage wheels 1206 may be seen. The carriage body 1301 serves as the chassis of the carriage 901; it is the frame on which the other parts are mounted. The cylindrical bearing 1204 is disposed in a mating hole in the carriage body 1301. The carriage body 1301 and the rotary mount 1201 are placed in frictional contact allowing the rotary mount 1201 to swivel. A platform section 1303 of the rotary mount 1201 is on top of the cylindrical bearing 1204, in relation to the carriage body 1301. The platform section 1303 functions as a base for the rotary platter 1101. The entire microplate transport carriage 901 rides on the carriage wheels 1206.

Also shown in FIG. 13 are the rails 1303 and the rail mount 1304 of the microplate transport rail assembly 902. Rail mount 1304 provides a support frame for the rails 1303 and also provides a mounting position for each travel sensor 1004a and rotation sensor 1004b. Performing this function, rail mount 1304 represents an end point for the microplate transport carriage 901 such that carriage 901 may be stopped with its center of rotation precisely aligned with the center line of rail mount 1304. Also, the rail mount 1304 acts as an articulated mount, allowing two systems interfaced by the microplate transport assembly to be articulated by up to 40°. The rail mount 1304 essentially functions as a homing position for both translation of the carriage 901 along the microplate rail assembly 902 and orientation of the rotary platter 1101 with respect to a foreign system (not shown) that may be interfacing with the present system. This structure cures any problems of physical connection if one of the stations is moved out of alignment.

Figure 14:
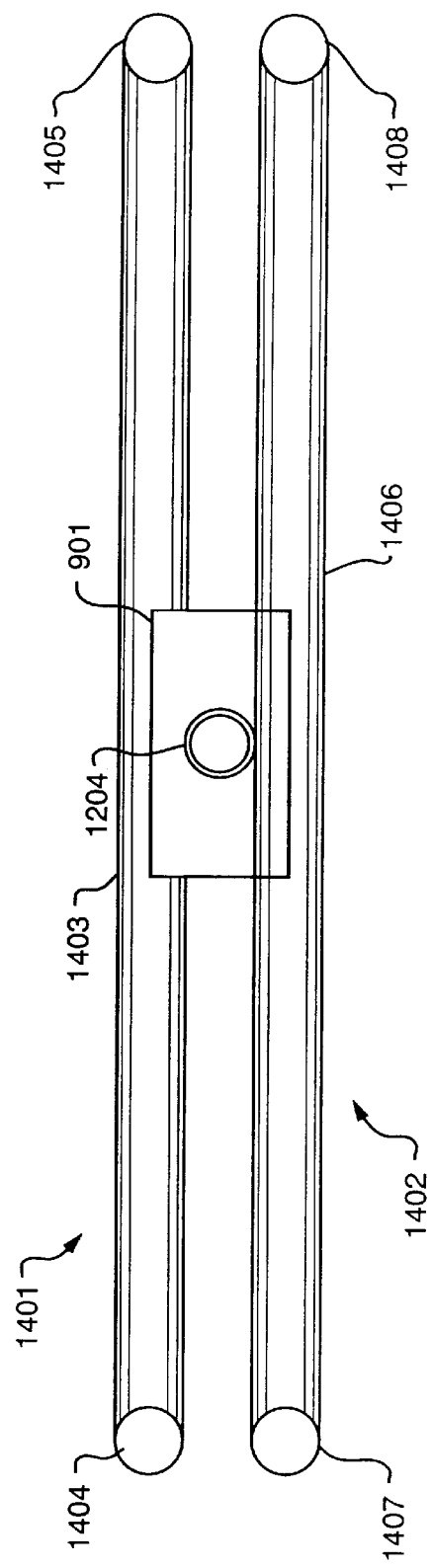
FIG. 14 is a cabling diagram shown the interconnection of the cables and servos of the microplate transport.

Referring to FIG. 14, a diagram of the cabling assembly is provided. The cabling assembly comprises a travel cable assembly 1401 and a rotary cable assembly 1402. Travel cable assembly 1401 connects the carriage 901 to the travel servo 1002a. The travel cable assembly 1401 comprises a length of travel cable 1403 that loops around a pulley 1404 on the travel servo 1002a and around a pulley 1405 that attaches to the opposite end, with respect to the travel servo 1002a, of the microplate transport rail assembly 902. The ends of the travel cable 1403 attach to the forward and aft ends of the carriage 901.

Similarly, rotary cable assembly 1402 comprises a length of rotary cable 1406 that loops around a pulley 1407 on the rotation servo 1002b and around a pulley 1408 on the opposite end of the transport rail assembly 902. In addition, the ends of the rotary cable 1406 loop around the cylindrical bearing 1204 of the rotary mount 1201 and are attached thereto. The movement of the rotary cable 1406 rotates the rotary platter 1101 when the carriage 901 is at rest, i.e. when it is not moving along the microplate transport rail assembly 902. The rotation servo 1002b rotates the rotary platter 1101 by pulling the loops around the rotary mount 1201. The loops are affected by operating the rotation servo 1002b in one direction or another while the carriage 901 is at rest. Those skilled in the art will recognize that the rotary platter may be rotated while the microplate transport carriage 901 is moving along the microplate transport rail assembly 902 by operating the travel servo 1002a and the rotation servo 1002b such that the travel cable 1403 and the rotary cable 1406 translate with respect to each other.

Figure 15A:
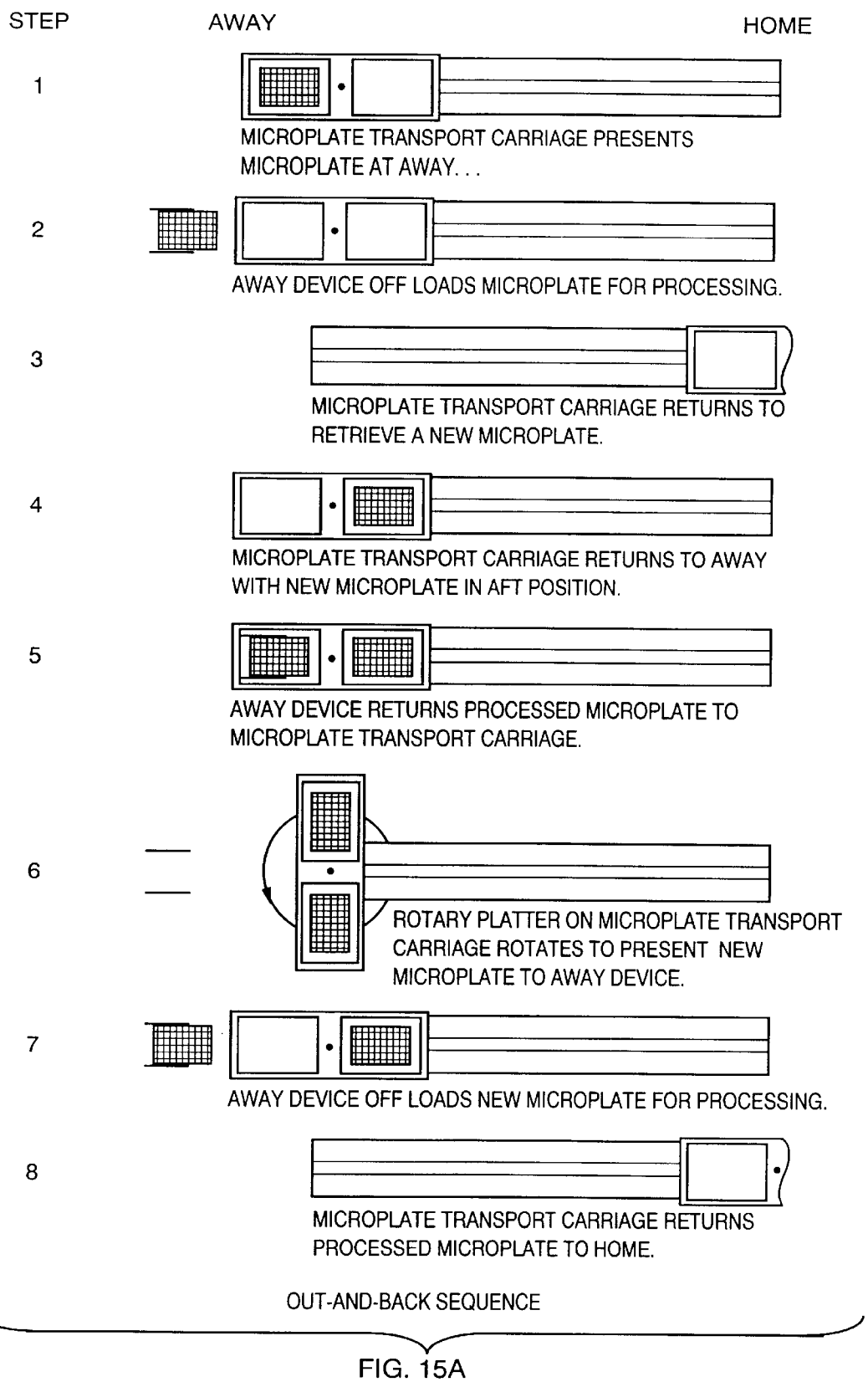

Referring to FIG. 15A, a slide-show illustrating a first method of operating carriage 901, which may be referred to as an "out-and-back" operation, is shown. The out-and-back method involves eight steps bringing microplates from one location, e.g home location, to another location for processing, e.g. away location. The carriage 901 carries the microplates between stations for processing and returns them to the home location after processing.

Figure 15B:
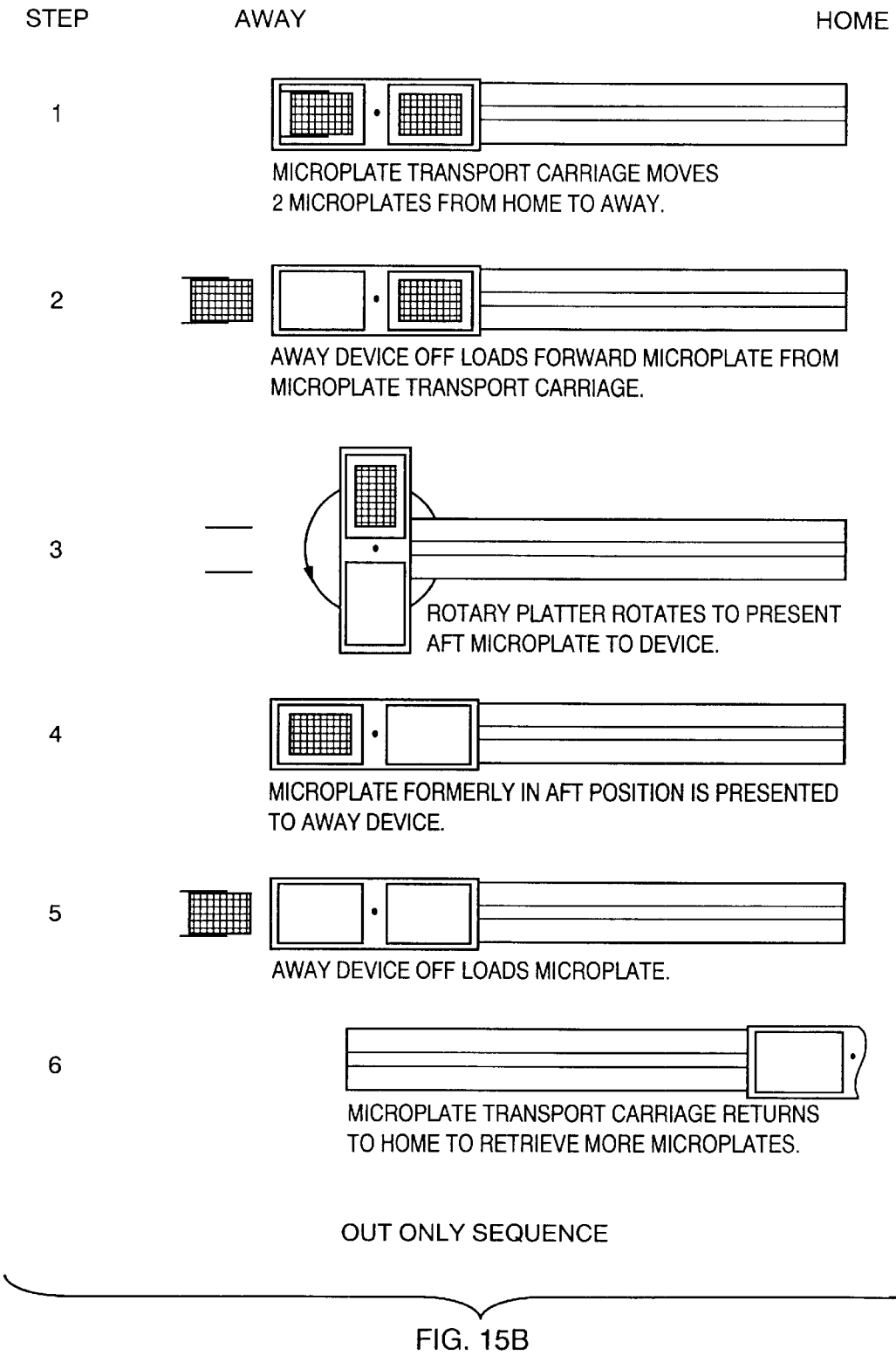

Referring to FIG. 15B, a slide-show illustrating a second method of operation, the "out only" method, is shown. The out only method may be used to move a plurality of microplates from one station to another, e.g. from home to away. Two microplates are loaded on the carriage 901 at home and transported to away. The rotary platter 1101 is used to rotate the microplate in the aft position, presenting it for off loading at the away location and for on loading the home location. The sequence involves six steps for each iteration. An iteration moves one set of microplates from the home location to the away location and returns the carriage 901 to the home location for loading.

Referring to FIG. 15C, a slide-show illustrating a third method of operation, the "pipette and wait" method, is shown. The pipette and wait method moves a microplate from one location, e.g. the home location, to another location, e.g. the away location, for pipetting. At the away location a pipette device, having a plurality of nozzles corresponding to the number of wells in a column of wells on the microplate, pipettes each of the wells in the microplate. The microplate transport carriage waits for completion of pipetting and then returns the microplate the home location.

Figure 16:
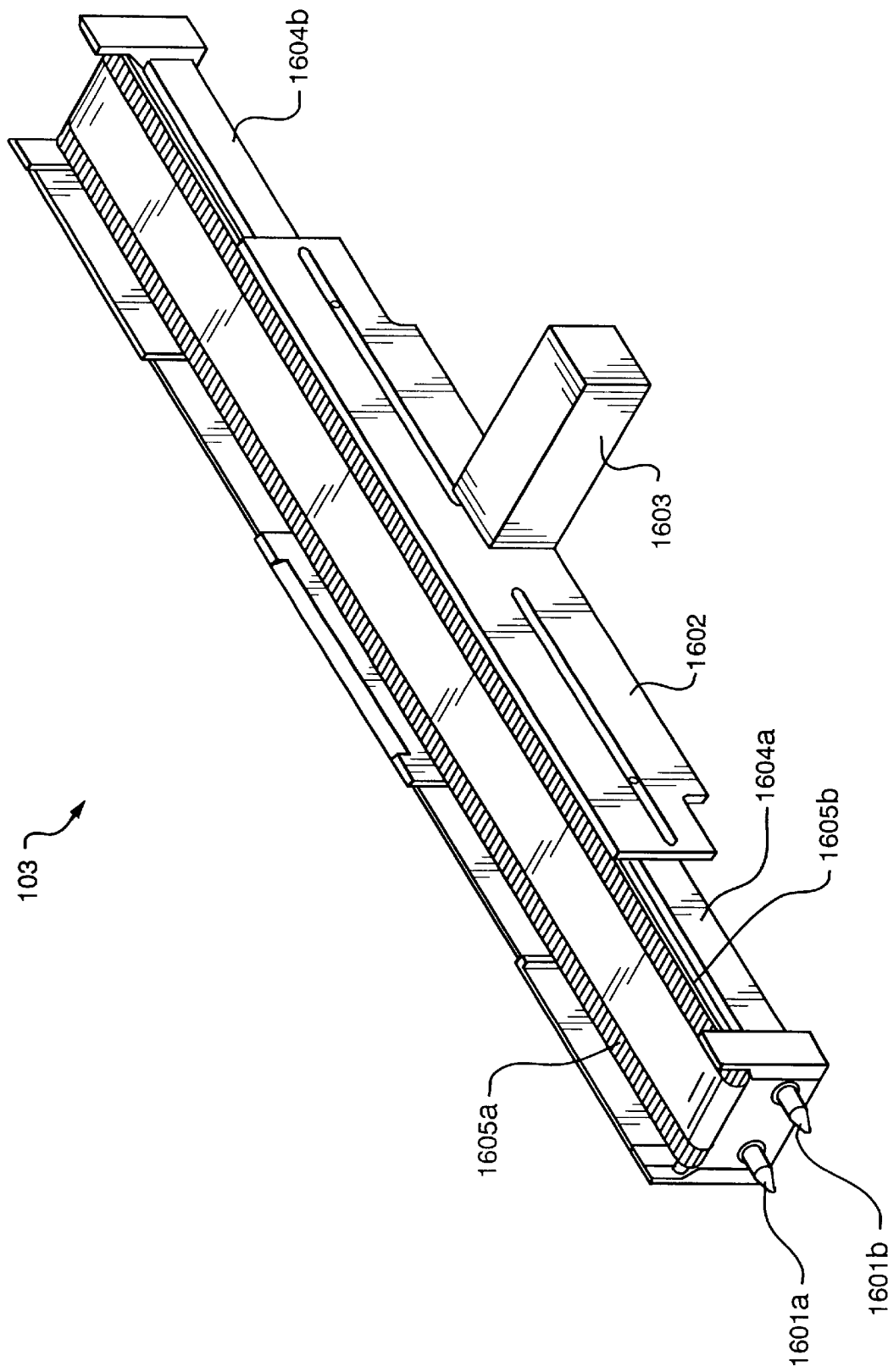
FIG. 16 is a perspective view of the microplate conveyor, separated from the cabinets it connects, shown in FIG. 1.

FIG. 16 shows microplate conveyor 103 (FIG. 1) in isolation. Two guidepins 1601a and 1601b extend laterally from one end of conveyor 103. Although not visible in this view, the opposite end of conveyor 103 preferably includes two guide holes which are dimensioned to receive guide pins 1601 from a second conveyor 103. A frame 1602 supports a motor housing 1603 and conveyor sections 1604a and 1604b. Two drive belts 1605a and 1605b extend along the length of conveyor 103. As may be seen best in FIGS. 18A and 18B, each drive belt 1605 is preferably a fixed length, endless loop passing through the interior of the conveyor. Conveyor 103 is preferably equipped with a suitable motor such that it may be driven in either direction.

Figure 17:
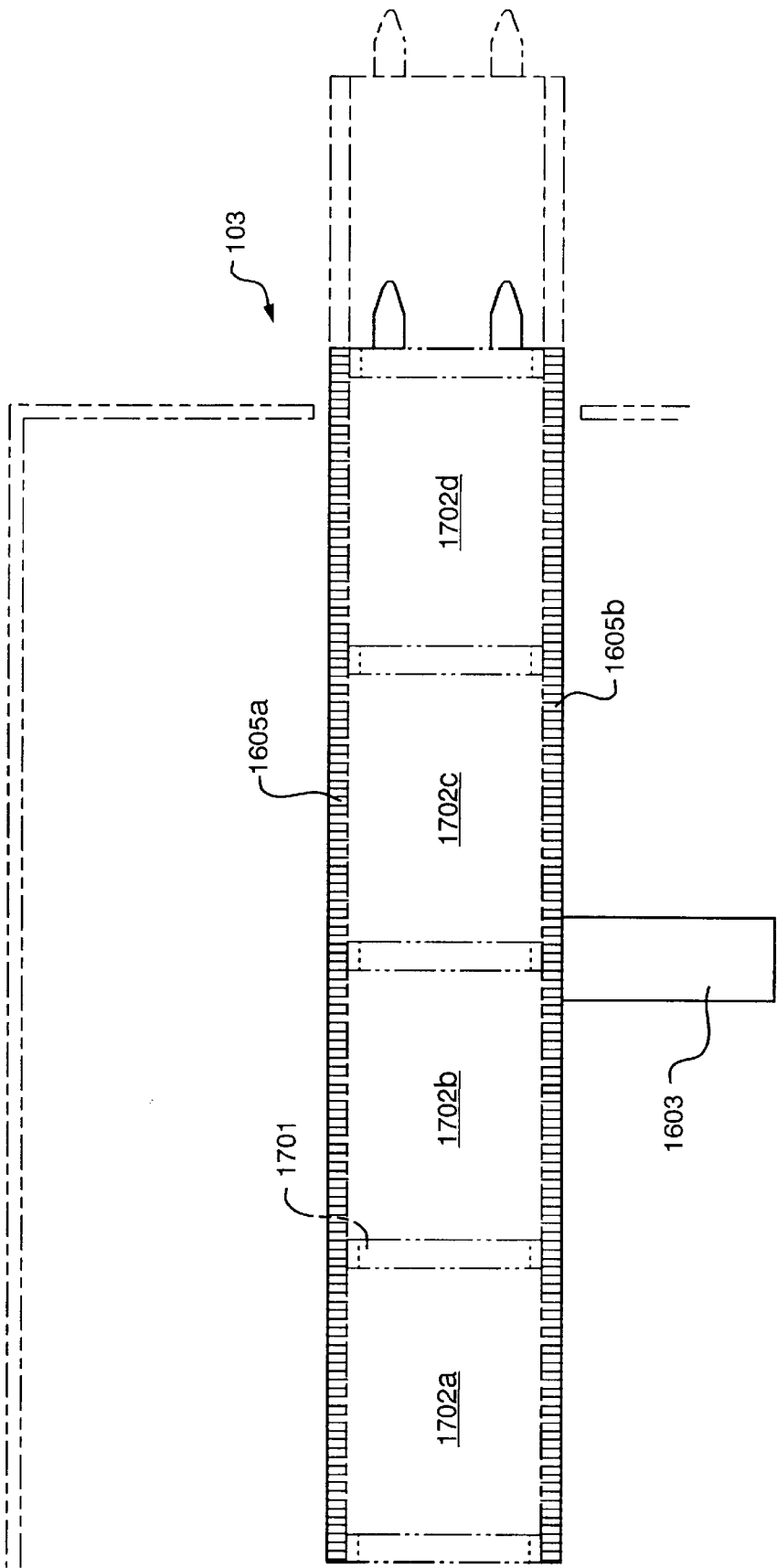
FIG. 17 is a top plan view of the microplate conveyor.

While shown in a fully extended position in FIG. 16, conveyor 103 is retractable or extendable as may be needed. For example, as may be seen in FIG. 17, conveyor 103 may be retracted into the interior of a cabinet (shown in phantom) until it is necessary to move microplates, at which time the conveyor is extended. Rather than place the microplates directly on the drive belts 1605, it is preferred that a microplate holder 1701 (shown in phantom) be placed on the drive belts with up to four microplates resting on top of the holder in positions 1702a–1702d.

Figure 18A:
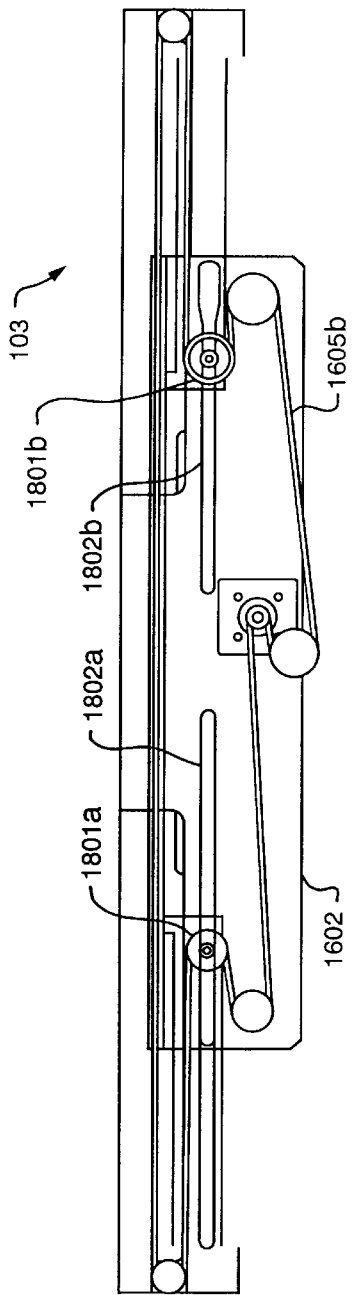
FIGS. 18A and 18B are cross sections showing the microplate conveyor in its retracted and extended positions.
Figure 18B:
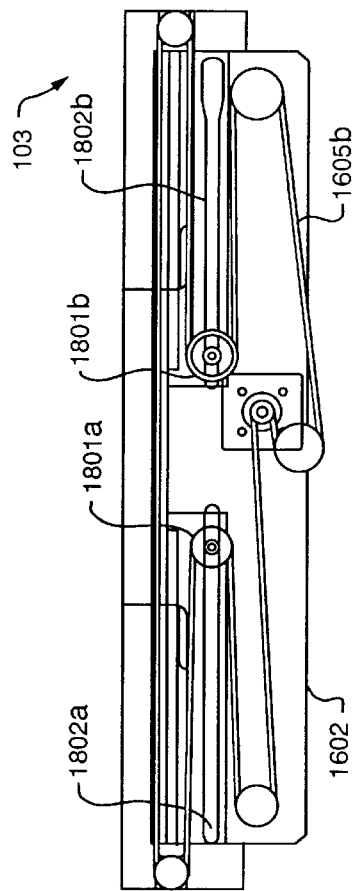

Referring now to FIGS. 18A and 18B, two movable tensioning pulleys 1801a and 1801b are disposed, respectively, in laterally extending slots 1802a and 1802b. When conveyor 103 is extended, as shown in FIG. 18A, pulleys 1801 move outward and apart, effectively providing slack on drive belts 1605 to accommodate the extension. Conversely, when conveyor 103 is retracted, pulleys 1801 move inward and toward each other, effectively taking in slack on drive belts 1605. As a result, drive belts 1605 may be advantageously manufactured as fixed length, endless loops which do not require adjustment to accommodate changes in the extension of conveyor 103.

What is claimed is:

1. Apparatus for random access storage and retrieval of a plurality of microplates, said apparatus comprising:

a plurality of microplate racks for storing microplates in assigned locations on said racks, said racks being arranged in a stack, each of said racks being mechanically engaged with a plurality of support columns for movement along said columns, each of said columns having a plurality of locking devices, corresponding to the plurality of racks, for locking selected racks to said columns;

a lift, coupled to said support columns, for longitudinal movement of said columns; and a controller, coupled to said lift and locking devices, responsive to a signal to access a desired microplate location to cause actuation of one or more of said locking devices to lock the rack adjacent to the rack containing desired location, followed by actuation of the lift, thereby moving a portion of the stack a sufficient distance to allow access to the desired microplate location.

2. The apparatus of claim 1 further comprising a transfer unit for moving selected microplates to and from the microplate racks, said transfer unit comprising an elevator;

a crawler supported by said elevator and carrying a microplate gripper; and means for moving said crawler toward and away from said stack;

whereby said elevator may position said crawler opposite the rack containing a desired microplate location and said craweler may be moved toward said stack to place a microplate in said desired location or retrieve a microplate from said location.

3. The apparatus of claim 2 in which:

each rack includes a pair of parallel rack rails;

the transport unit includes: a pair of transport unit rails supported on said elevator, said crawler being mounted on said transport unit rails for movement therealong toward and away from said stack, means for juxtaposing said transport unit rails with the rack rails of a rack having a selected microplate location, whereby said rack rails become extensions of said transport unit rails, and means for moving said crawler along said transport unit rails and said rack rails to position said gripper for access to the selected microplate location.

4. The apparatus of claim 3 in which said rails are toothed racks and said moving means includes pinions on said crawler that engaged the rack teeth.

5. The apparatus defined in claim 1 in which:

said locking devices are plungers mounted on at least one of said columns; and each rack includes meanings forming a hole opposite a plunger associated with that rack;

whereby actuation of a plunger causes insertion of a pin into the hole, thereby securing the rack against movement relative to the columns.

* * * * *